(12) United States Patent
Barker

(10) Patent No.: US 8,768,488 B2
(45) Date of Patent: Jul. 1, 2014

(54) SYSTEMS AND METHODS FOR ELECTRICALLY STIMULATING PATIENT TISSUE ON OR AROUND ONE OR MORE BONY STRUCTURES

(71) Applicant: Boston Scientific Neuromodulation Corporation, Valencia, CA (US)

(72) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/899,350

(22) Filed: May 21, 2013

(65) Prior Publication Data

US 2013/0317585 A1 Nov. 28, 2013

Related U.S. Application Data

(60) Provisional application No. 61/651,840, filed on May 25, 2012.

(51) Int. Cl.
*A61N 1/00* (2006.01)
(52) U.S. Cl.
USPC .......................................................... 607/117
(58) Field of Classification Search
CPC .................................................. A61N 1/0558
USPC ......................................................... 607/117
See application file for complete search history.

(56) References Cited

U.S. PATENT DOCUMENTS

| | | | |
|---|---|---|---|
| 3,918,440 A | 11/1975 | Kraus | |
| 5,330,477 A | 7/1994 | Crook | |
| 5,738,521 A | 4/1998 | Dugot | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |

(Continued)

FOREIGN PATENT DOCUMENTS

| AU | 2012201634 A1 | 4/2012 |
|---|---|---|
| WO | WO-03020365 A1 | 3/2003 |

(Continued)

OTHER PUBLICATIONS

International Application No. PCT/US2013/042014, International Search Report & Written Opinion mailed Sep. 26, 2013.

(Continued)

*Primary Examiner* — Robert N Wieland
(74) *Attorney, Agent, or Firm* — Lowe Graham Jones PLLC; Patrick R. Turner

(57) ABSTRACT

An implantable lead assembly for providing electrical stimulation to a patient includes a lead body; a terminal disposed along a proximal end of the lead body; and an orthopedic implant coupled to a distal end of the lead body. The orthopedic implant is configured and arranged for anchoring to a bony structure. At least one mounting region is disposed along the orthopedic implant. The at least one mounting region is configured and arranged for anchoring the orthopedic implant to the at least one bony structure. An electrode is disposed along a stimulation region of the orthopedic implant. A conductor electrically couples the terminal to the electrode.

20 Claims, 17 Drawing Sheets

(56) References Cited

U.S. PATENT DOCUMENTS

| | | |
|---|---|---|
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,295,944 B2 | 10/2012 | Howard et al. |
| 8,364,278 B2 | 1/2013 | Pianca et al. |
| 8,391,985 B2 | 3/2013 | McDonald |
| 2005/0033374 A1 | 2/2005 | Gerber |
| 2007/0150036 A1 | 6/2007 | Anderson |
| 2007/0265682 A1* | 11/2007 | Wiegmann et al. ............ 607/51 |
| 2008/0140169 A1 | 6/2008 | Imran |
| 2010/0268298 A1 | 10/2010 | Moffitt et al. |
| 2010/0274336 A1 | 10/2010 | Nguyen-Stella et al. |
| 2011/0005069 A1 | 1/2011 | Pianca |
| 2011/0078900 A1 | 4/2011 | Pianca et al. |
| 2011/0130817 A1 | 6/2011 | Chen |
| 2011/0130818 A1 | 6/2011 | Chen |
| 2011/0178573 A1 | 7/2011 | Nguyen-Stella et al. |
| 2011/0238129 A1 | 9/2011 | Moffitt et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0317583 A1 | 11/2013 | Pianca |
| 2013/0317586 A1 | 11/2013 | Pianca |
| 2013/0317587 A1 | 11/2013 | Barker |
| 2013/0317588 A1 | 11/2013 | Howard et al. |

FOREIGN PATENT DOCUMENTS

| | | |
|---|---|---|
| WO | WO-03084398 A1 | 10/2003 |
| WO | 2005120203 A2 | 12/2005 |
| WO | WO-2005120203 A2 | 12/2005 |
| WO | WO-2006029257 A2 | 3/2006 |
| WO | 2007041604 A2 | 4/2007 |
| WO | WO-2007041604 A2 | 4/2007 |
| WO | WO-2010083308 A1 | 7/2010 |

OTHER PUBLICATIONS

U.S. Appl. No. 61/651,815, filed May 25, 2012.
U.S. Appl. No. 13/939,900, filed Jul. 11, 2013.

\* cited by examiner

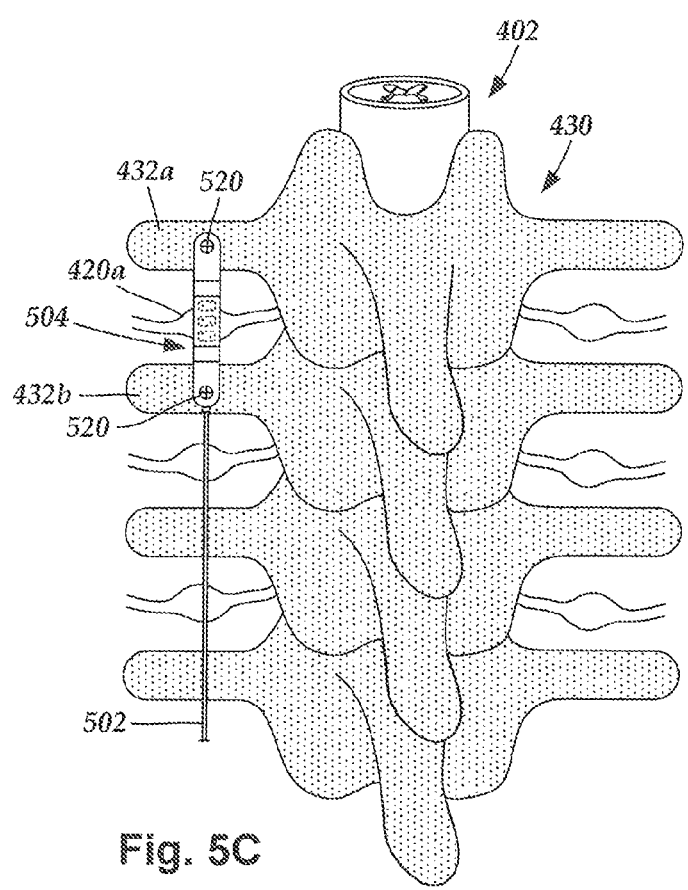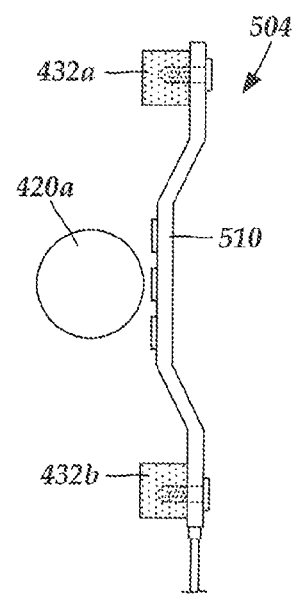
Fig. 5C
Fig. 5D

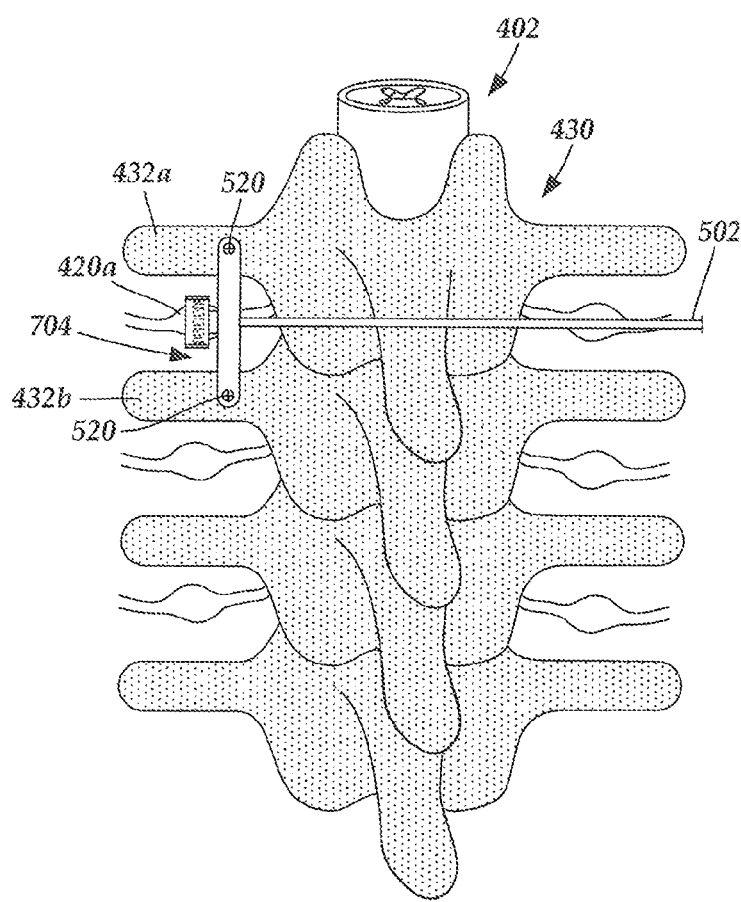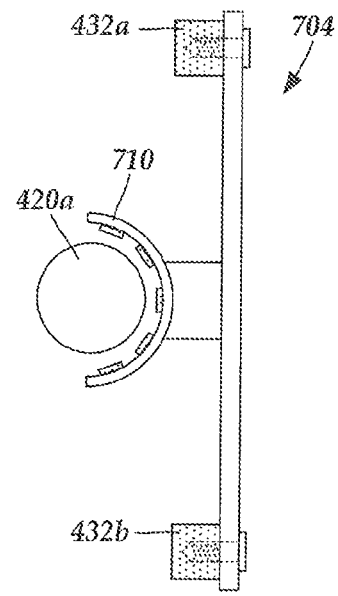
Fig. 7C
Fig. 7D

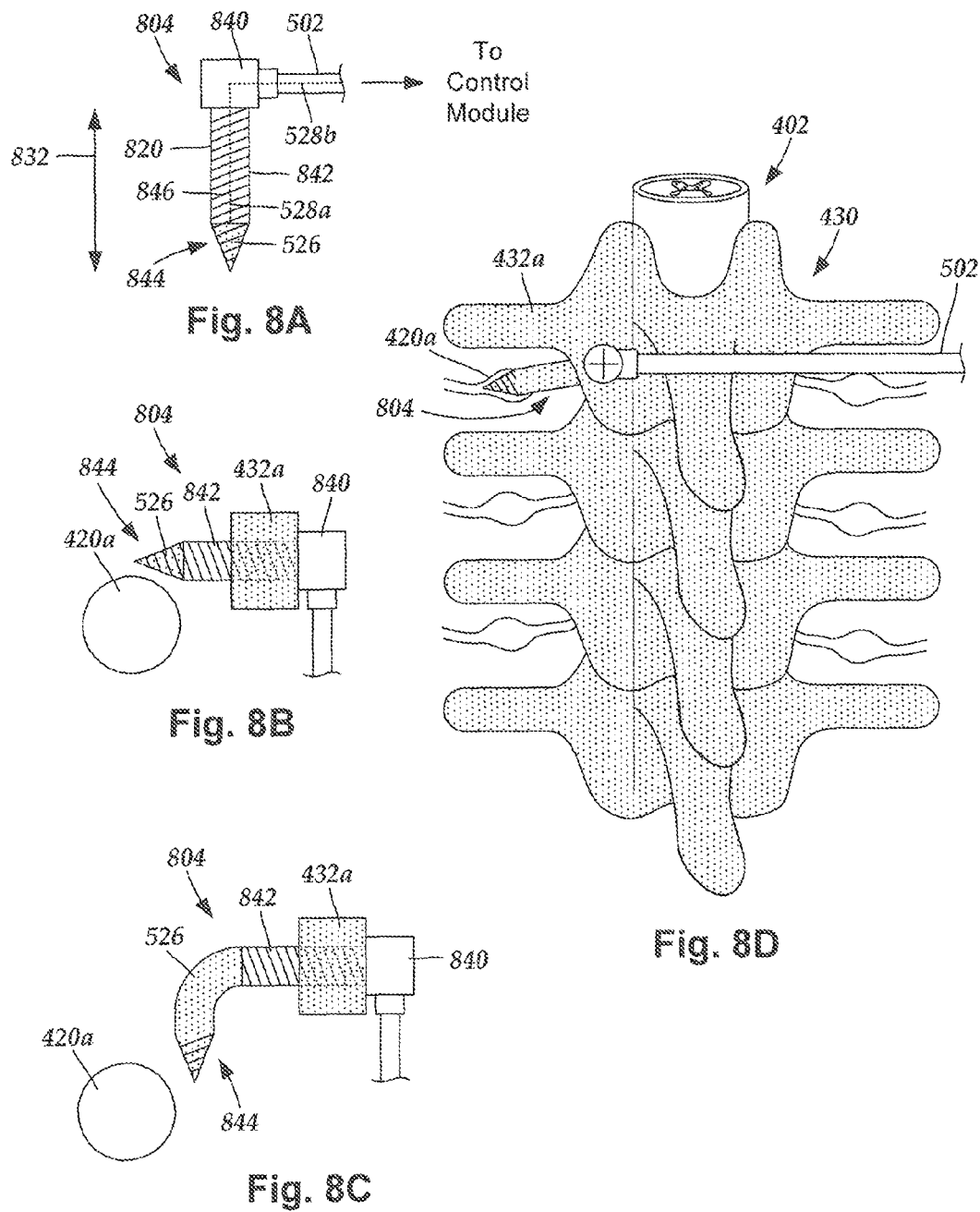

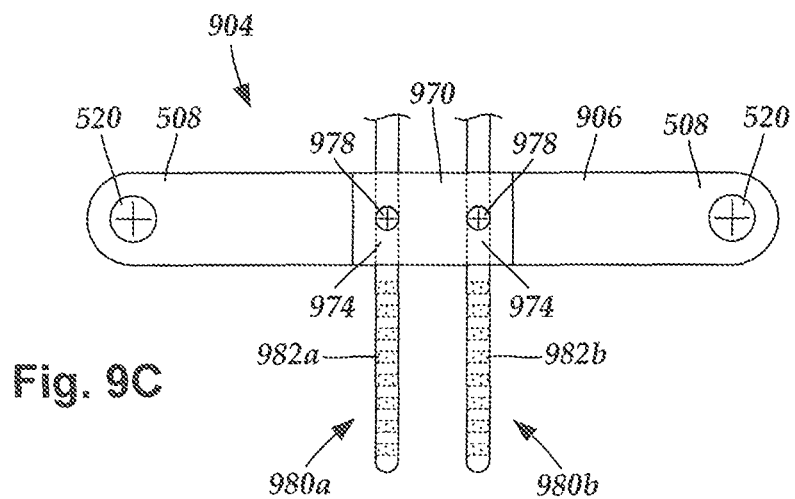
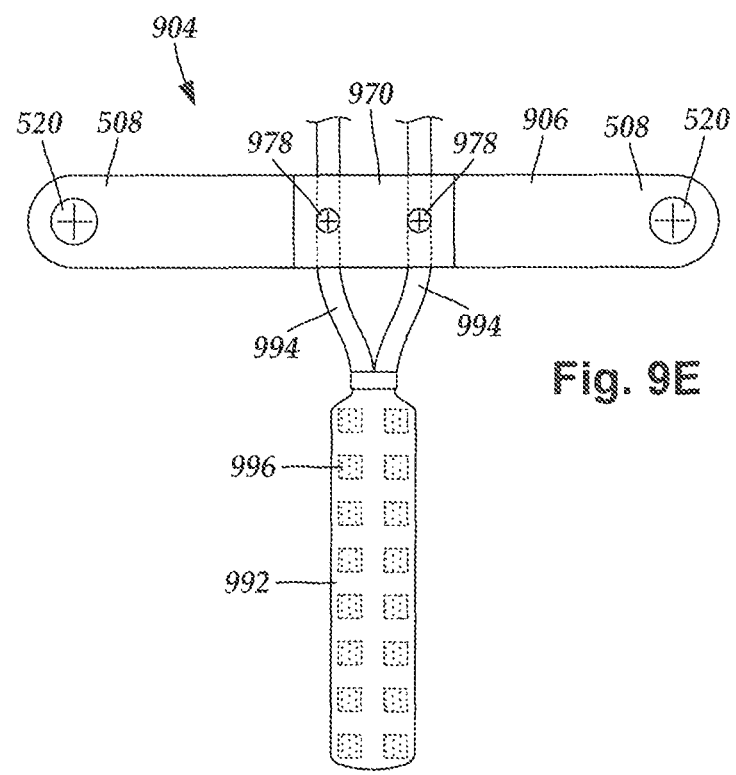

SYSTEMS AND METHODS FOR ELECTRICALLY STIMULATING PATIENT TISSUE ON OR AROUND ONE OR MORE BONY STRUCTURES

CROSS-REFERENCE TO RELATED APPLICATIONS

This application claims the benefit under 35 U.S.C. §119 (e) of U.S. Provisional Patent Application Ser. No. 61/651,840 filed on May 25, 2012, which is incorporated herein by reference.

FIELD

The present invention is directed to the area of implantable electrical stimulation systems and methods of making and using the systems. The present invention is also directed to implantable electrical stimulation leads configured and arranged for anchoring to one or more bony structures in proximity to a target stimulation region, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Dorsal root ganglia are nodules of cell bodies disposed along the dorsal roots of spinal nerves. Dorsal root ganglia are disposed external to the epidural space. Dorsal root ganglia, however, are disposed in proximity to the spinal cord and the vertebral column.

BRIEF SUMMARY

In one embodiment, an implantable lead assembly for providing electrical stimulation to a patient includes a lead body having a proximal end, a distal end, and a longitudinal length; at least one terminal disposed at the proximal end of the lead body; and an orthopedic implant coupled to the distal end of the lead body. The orthopedic implant is configured and arranged for anchoring to at least one bony structure. The orthopedic implant includes an elongated orthopedic implant body having a first end and an opposing second end. At least one mounting region is disposed along the orthopedic implant body. The at least one mounting region is configured and arranged for anchoring the orthopedic implant to the at least one bony structure. At least one stimulation region is disposed along the orthopedic implant body. At least one electrode is disposed along the at least one stimulation region. At least one conductor electrically couples the at least one terminal to the at least one electrode.

In another embodiment, a lead anchoring assembly for providing electrical stimulation includes an orthopedic implant configured and arranged to receive a distal end of a lead body of a first lead. The orthopedic implant is configured and arranged for anchoring to at least one bony structure. The orthopedic implant includes an orthopedic implant body having a first end, a second end opposite to the first end, a first side, a second side opposite to the first side, a top surface, and a bottom surface opposite to the top surface. At least one mounting region is disposed along the first end of the orthopedic implant body. The at least one mounting region is configured and arranged for anchoring the orthopedic implant to the at least one bony structure. A lead anchoring region is disposed along the orthopedic implant body. The lead anchoring region is configured and arranged for receiving the first lead and for fastening the first lead to the orthopedic implant.

In yet another embodiment, an implantable lead assembly for providing electrical stimulation to a patient includes a lead body having a proximal end, a distal end, and a longitudinal length; at least one terminal disposed at the proximal end of the lead body; and an orthopedic implant coupled to the distal end of the lead body. The orthopedic implant is configured and arranged for anchoring to at least one bony structure. The orthopedic implant includes a head configured and arranged for receiving a fastening tool. An elongated shaft is coupled to the head. The shaft has a first end and an opposing second end. The first end couples to the head. A tip is disposed on the second end of the shaft. The tip is configured and arranged to anchor to the at least one bony structure. At least one electrode is disposed along the tip of the orthopedic implant. At least one conductor electrically couples the at least one terminal to the at least one electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5C is a schematic top view of one embodiment of the orthopedic implant of FIG. 5A anchored to two of the vertebrae of FIG. 4B, according to the invention;

FIG. 5D is a schematic side view of one embodiment of the orthopedic implant of FIG. 5A anchored to two of the vertebrae of FIG. 4B, according to the invention;

FIG. 7C is a schematic top view of one embodiment of the orthopedic implant of FIG. 7A anchored to two of the vertebrae of FIG. 4B, according to the invention;

FIG. 7D is a schematic side view of one embodiment of the orthopedic implant of FIG. 7A anchored to two of the vertebrae of FIG. 4B, according to the invention;

FIG. 8A is a schematic side view of a fourth embodiment of an orthopedic implant suitable for anchoring to one of the vertebrae of FIG. 4B, according to the invention;

FIG. 8B is a schematic side view of one embodiment of the orthopedic implant of FIG. 8A anchored to one of the vertebrae of FIG. 4B, according to the invention;

FIG. 8C is a schematic side view of another embodiment of the orthopedic implant of FIG. 8A anchored to one of the vertebrae of FIG. 4B, the orthopedic implant having a bendable electrode, according to the invention;

FIG. 8D is a schematic top view of one embodiment of the orthopedic implant of FIG. 8C anchored to one of the vertebrae of FIG. 4B, according to the invention;

FIG. 9C is a schematic top view of one embodiment of two percutaneous leads fastened to the orthopedic implant of FIG. 9A, according to the invention;

FIG. 9E is a schematic top view of one embodiment of a paddle lead fastened to the orthopedic implant of FIG. 9A, according to the invention.

DETAILED DESCRIPTION

The present invention is directed to the area of implantable electrical stimulation systems and methods of making and using the systems. The present invention is also directed to implantable electrical stimulation leads configured and arranged for anchoring to one or more bony structures in proximity to a target stimulation region, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
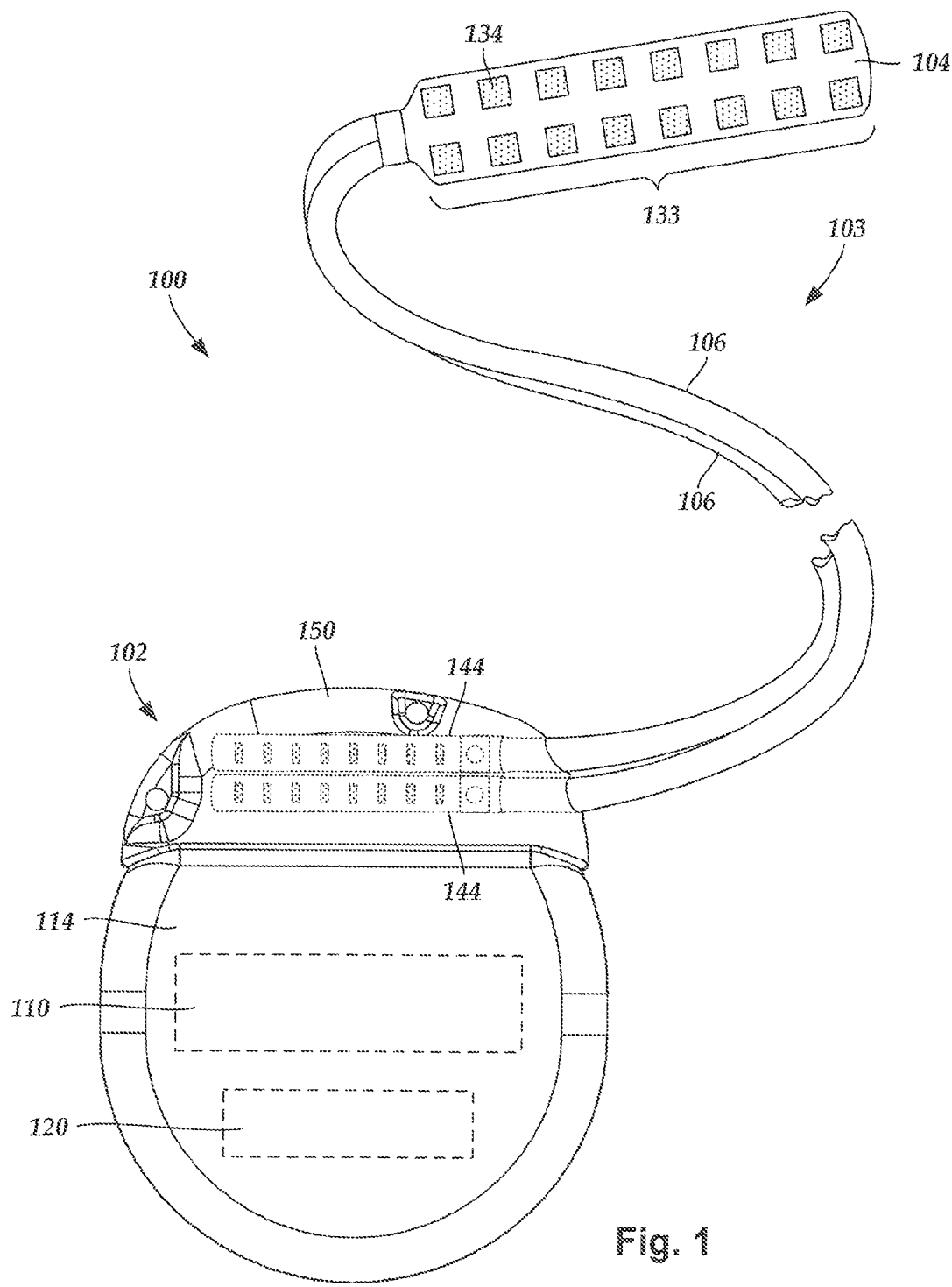
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102 and a lead 103. The lead 103 including a paddle body 104 and one or more lead bodies 106 coupling the control module 102 to the paddle body 104. The paddle body 104 and the one or more lead bodies 106 form the lead 103. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
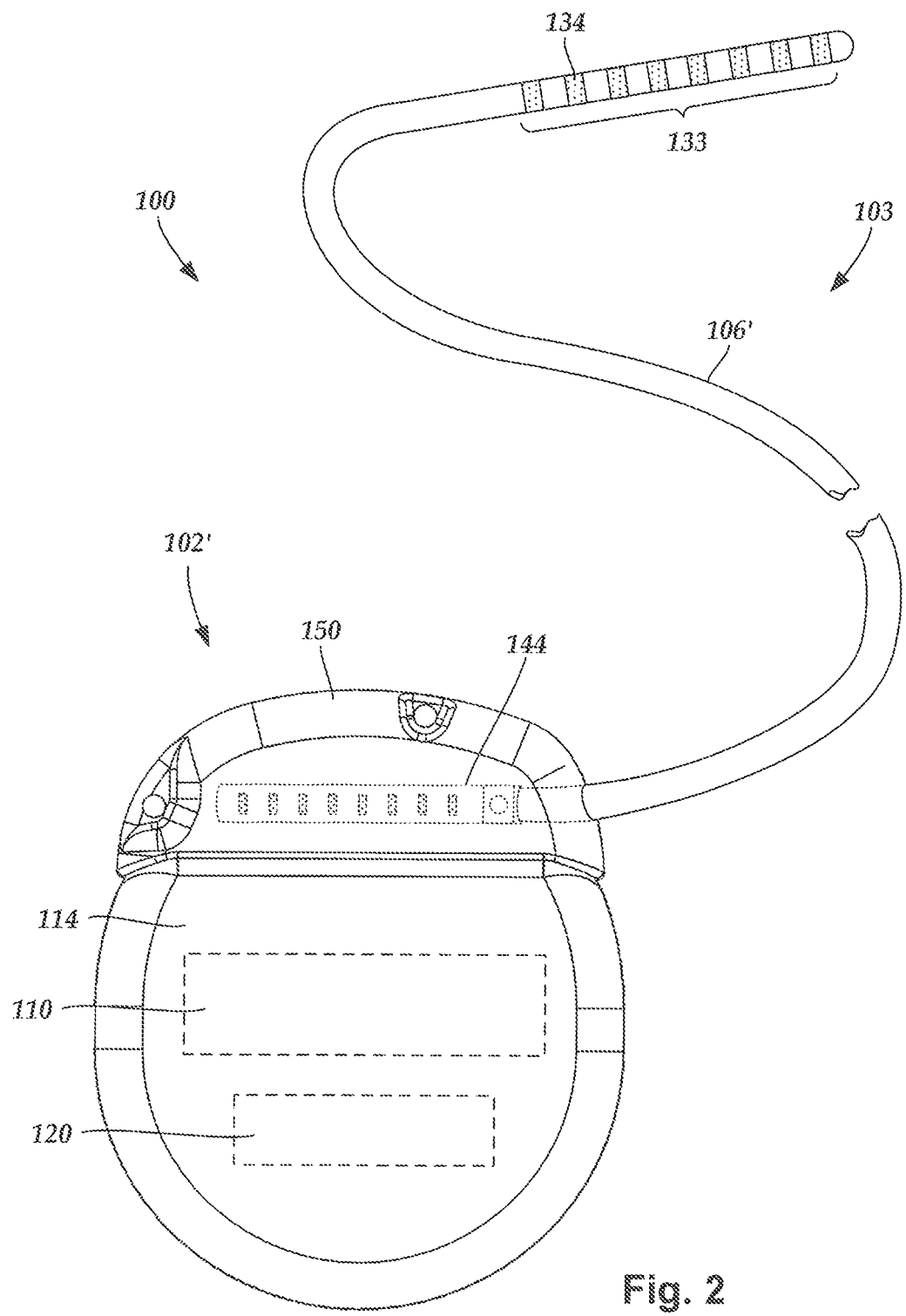
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead 103, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead 103 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
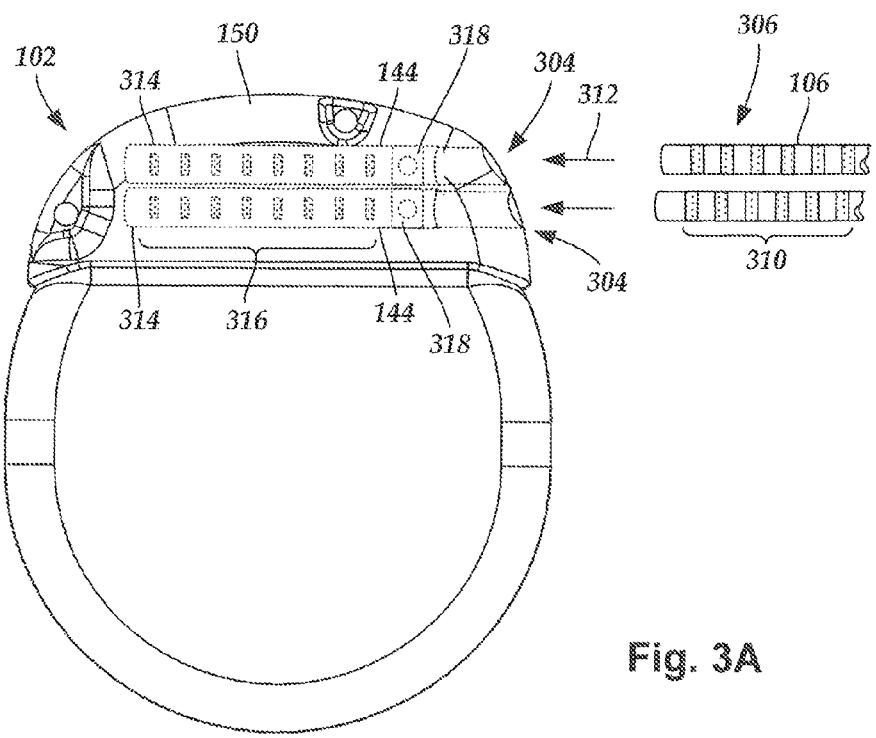
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
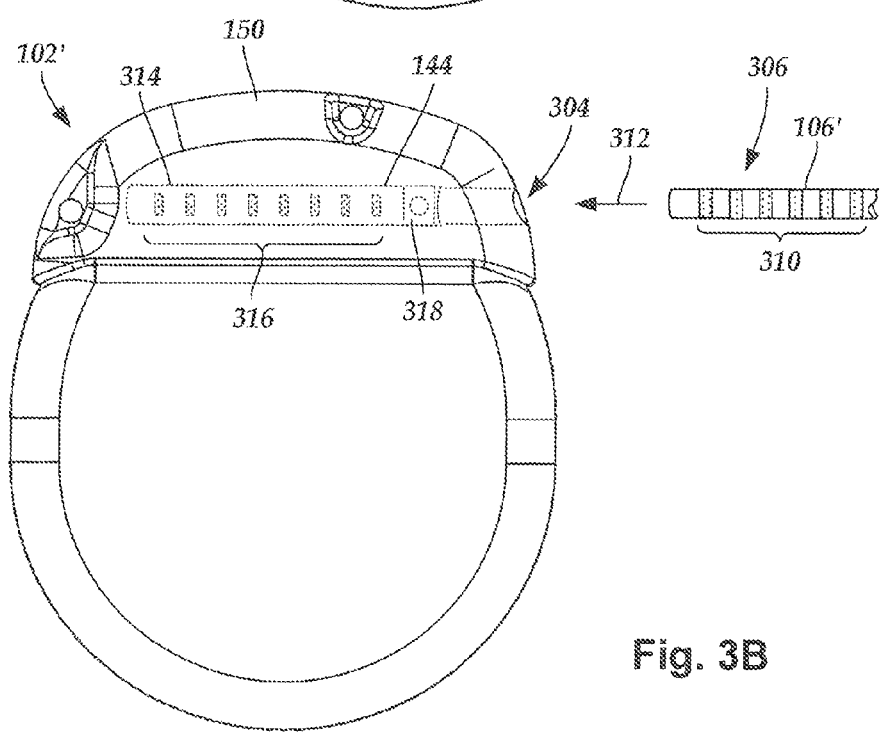
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture 320 through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
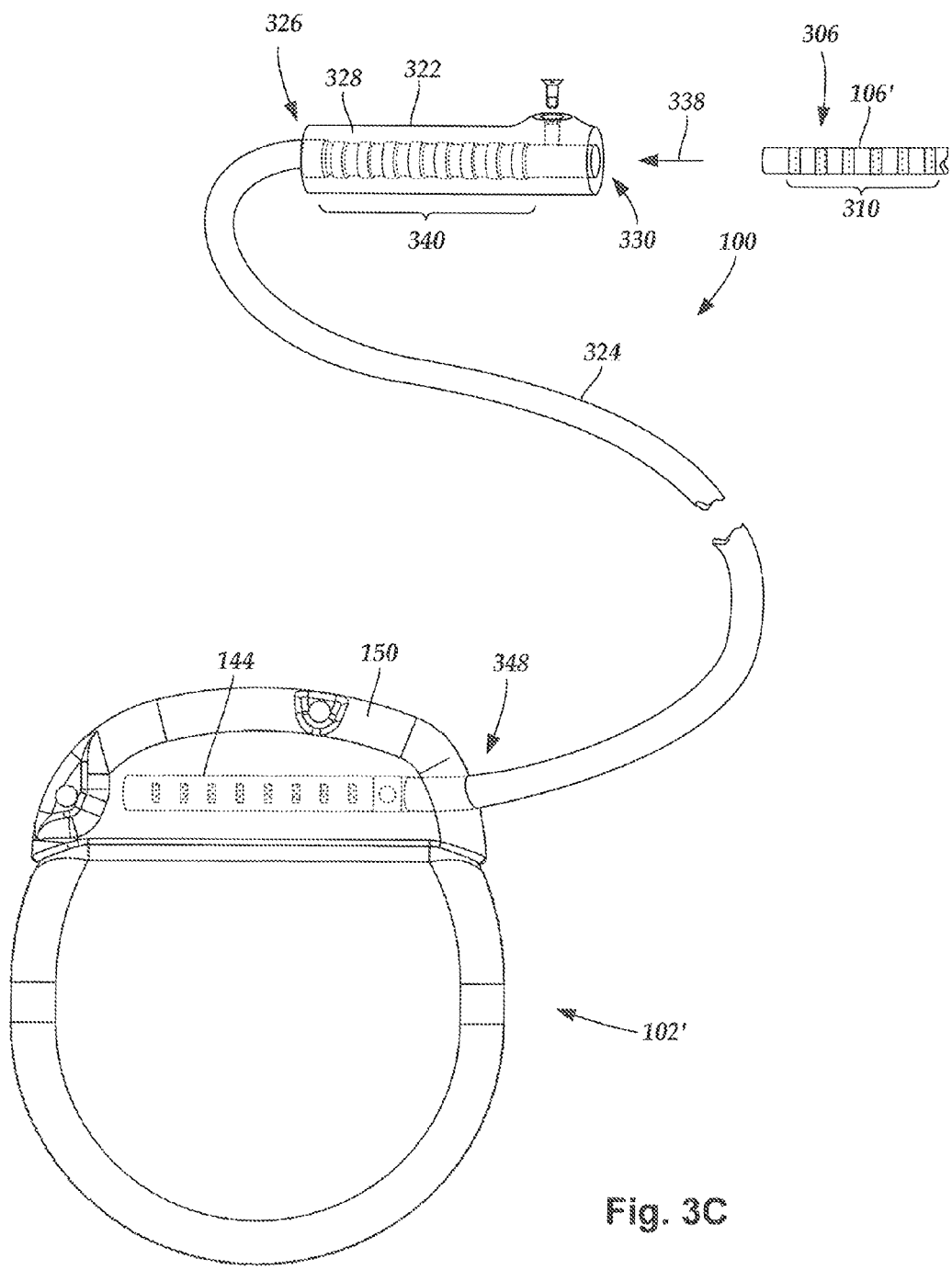
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Figure 4A:
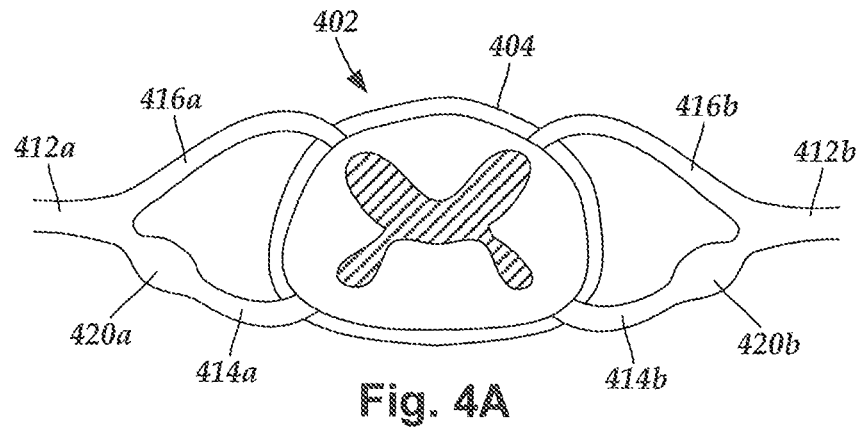
FIG. 4A is a schematic transverse cross-sectional view of spinal nerves extending from a spinal cord, the spinal nerves including dorsal root ganglia.

Turning to FIG. 4A, some target stimulation locations are located in proximity to one or more bony structures. When stimulating a region in proximity to one or more bony structures, it may be desirable to anchor the lead to the bony structure in order to prevent migration of the distal end of the lead which, in at least some cases, may disrupt efficacious stimulation.

One potential target stimulation location in proximity to a bony structure is the dorsal root ganglia. FIG. 4A schematically illustrates a transverse cross-sectional view of a spinal cord 402 surrounded by dura 404. The spinal cord 402 includes a plurality of levels from which spinal nerves 412a and 412b extend. In at least some spinal cord levels, the spinal nerves 412a and 412b extend bilaterally from the spinal cord 402. In FIG. 4A, the spinal nerves 412a and 412b attach to the spinal cord 402 via corresponding dorsal roots 414a and 414b and corresponding ventral (or anterior) roots 416a and 416b. Typically, the dorsal roots 414a and 414b relay sensory information into the spinal cord 402 and the ventral roots 416a and 416b relay motor information outward from the spinal cord 402. Dorsal root ganglia ("DRG") 420a and 420b are nodules of cell bodies that are disposed along the dorsal roots 416a and 416b in proximity to the spinal cord 402.

Figure 4B:
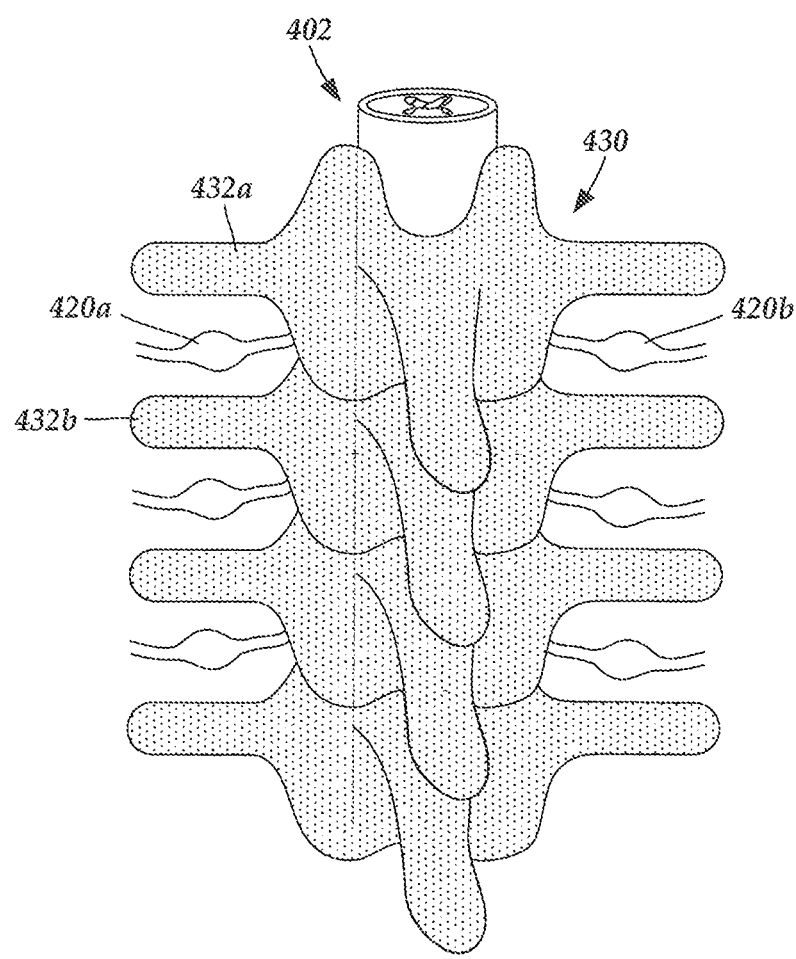
FIG. 4B is a schematic perspective view of a portion of the spinal cord of FIG. 4A disposed in a portion of a vertebral column with the dorsal root ganglia of FIG. 4A extending outward from the vertebral column.

FIG. 4B schematically illustrates a perspective view of a portion of the spinal cord 402 disposed along a portion of a vertebral column 430. The vertebral column 430 includes a plurality of stacked vertebrae, such as vertebrae 432a and 432b, and a plurality of DRGs 420a and 420b extending outwardly bilaterally from the spinal cord 402.

Figure 4C:
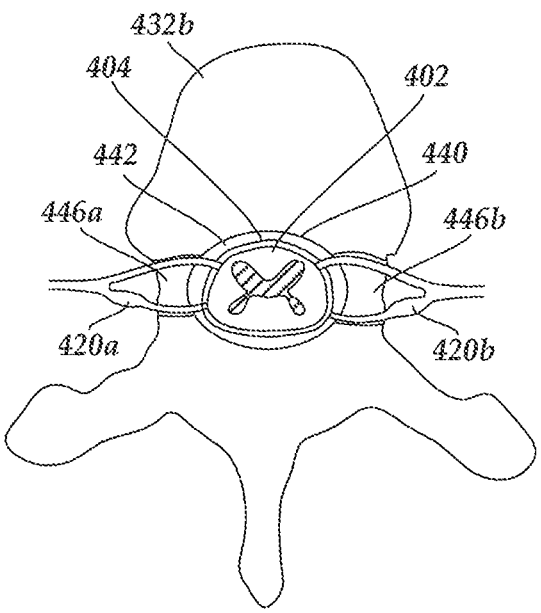
FIG. 4C is a schematic top view of a portion of the spinal cord of FIG. 4A disposed in a vertebral foramen defined in a vertebra of the vertebral column of FIG. 4B, the vertebra also defining intervertebral foramina extending between an outer surface of the vertebra and the vertebral foramen, the intervertebral foramina providing an opening through which the dorsal root ganglia of FIG. 4B can extend outward from the spinal cord of FIG. 4B.

FIG. 4C schematically illustrates a top view of a portion of the spinal cord 402 and dura 404 disposed in a vertebral foramen 440 defined in the vertebra 432b. The vertebrae, such as the vertebrae 432a and 432b, are stacked together and the vertebral foramina 440 of the vertebrae collectively form a spinal canal through which the spinal cord 402 extends. The space within the spinal canal between the dura 404 and the walls of the vertebral foramen 440 defines the epidural space 442. Intervertebral foramina 446a and 446b, defined bilaterally along sides of the vertebra 432b, form openings through the vertebra 432b between the epidural space 442 and the environment external to the vertebra 432b.

Figure 4D:
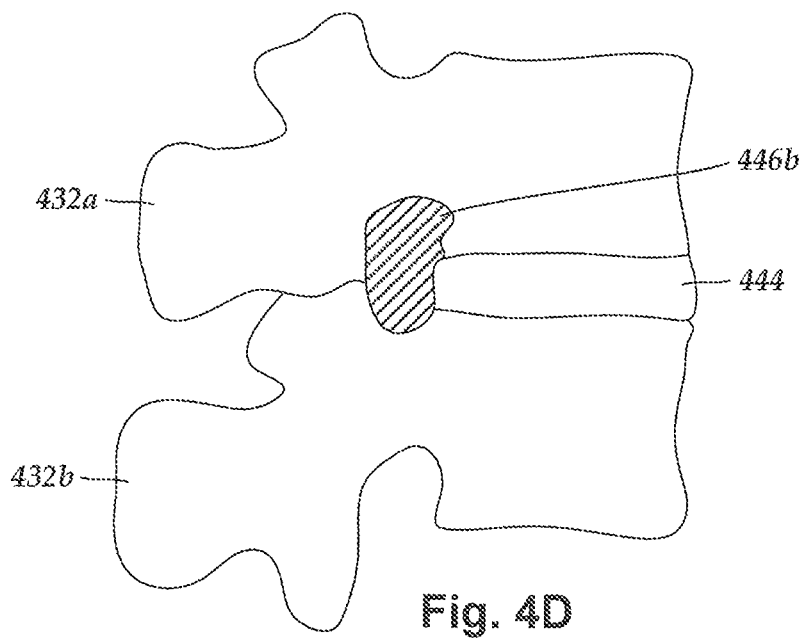
FIG. 4D is a schematic side view of two vertebrae of the vertebral column of FIG. 4B, the vertebrae defining an intervertebral foramen through which the dorsal root ganglia of FIG. 4B can extend outward from the spinal cord of FIG. 4B.

FIG. 4D schematically illustrates a side view of two vertebrae 432a and 432b coupled to one another by a disc 444. In FIG. 4D, the intervertebral foramen 446b is shown defined between the vertebrae 432a and 432b. The intervertebral foramen 446b provides an opening for one or more of the dorsal root 414b, ventral root 416b, and DRG 420b to extend outwardly from the spinal cord 402.

Figure 5A:
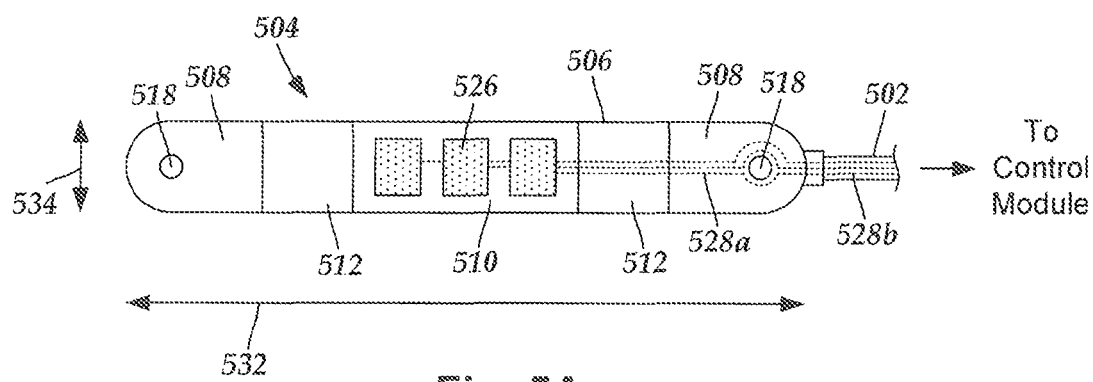
FIG. 5A is a schematic bottom view of one embodiment of an orthopedic implant suitable for anchoring to one or more of the vertebrae of FIG. 4B, according to the invention.

Turning to FIG. 5A, as herein described one or more leads can be anchored to one or more bony structures in proximity to a target stimulation location. In at least some embodiments, the one or more leads are anchored to one or more vertebrae in proximity to the target stimulation location. It will be understood that the systems and methods discussed herein may be applicable to other bony structures of the patient including, for example, the skull, pelvis, scapulae, humerus, femur, or the like. In at least some embodiments, the target stimulation location is the DRG. It will be understood that the systems and methods discussed herein may be applicable to other target stimulation locations within the patient including, for example, other portions of the sensory nerves (e.g., the dorsal root or the ventral root), or other patient tissue in proximity to one or more other bony structures, besides the vertebrae.

Individuals with spinal orthopedic ailments may receive one or more orthopedic implants (e.g., rods, plates, straps, screws, or the like or combinations thereof) to provide therapy to the patient. In some cases, the orthopedic implants may span between two or more bony structures. For example, the orthopedic implant may span between two or more of the patient's vertebrae at a particular spinal cord level. In at least some embodiments, the one or more leads can be coupled to the one or more orthopedic implants such that the electrodes of the one or more lead are disposed on the orthopedic implant. In which case, the electrodes can be disposed along the orthopedic implant such that the electrodes are positioned in proximity to a target stimulation location in proximity to the one or more bony structures at the particular spinal cord level, such as the particular DRG disposed in proximity to the spinal cord level across which the orthopedic implant spans.

Orthopedic implants can be implanted into the patient in any suitable manner including, for example, using a series of hollow introducers. Further description of a series of hollow introducers can be found in U.S. Provisional Patent Application Ser. No. 61/651,815, incorporated herein by reference.

Figure 5B:
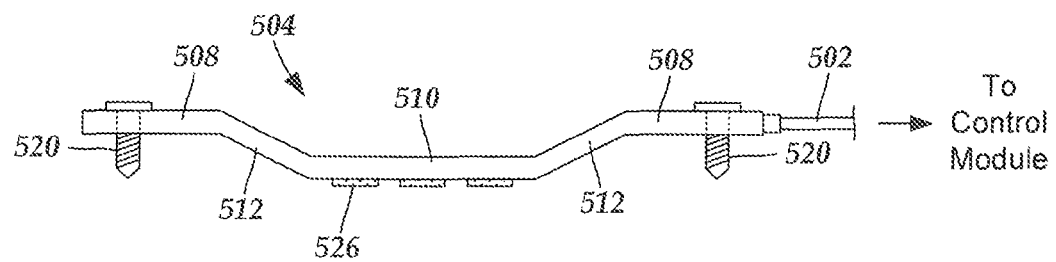
FIG. 5B is a schematic side view of one embodiment of the orthopedic implant of FIG. 5A, according to the invention.

FIG. 5A is a schematic bottom view of one embodiment of a distal end of a body of a lead 502 coupled to an orthopedic implant 504. FIG. 5B is a schematic side view of one embodiment of the distal end of the body of the lead 502 coupled to the orthopedic implant 504. The lead 502 includes a plurality of terminals (see e.g., terminals 310 of FIGS. 3A-3C) disposed along a proximal end of the body of the lead 502. The terminals are configured and arranged for electrically coupling with the control module (see e.g., 102 in FIG. 1) either directly, or via one or more intermediate components, such as a lead extension (see e.g., 324 of FIG. 3C).

The orthopedic implant 504 includes an elongated body 506 with one or more mounting regions 508 and one or more stimulation regions 510. In FIGS. 5A-5B, the body 506 is shown with two mounting regions 508 disposed on opposing ends of the body 506. In at least some embodiments, the one or more stimulation regions 510 are disposed between two or more mounting regions 508.

In at least some embodiments, the one or more mounting regions 508 are coupled to the one or more stimulation regions 510 via one or more transition regions 512. In at least some embodiments, the one or more mounting regions 508 are planar. In at least some embodiments, the one or more stimulation regions 510 are planar. In FIGS. 5A-5B, the mounting regions 508 and the stimulation region 510 are shown extending parallel to one another, while the transition regions 512 are shown as bent, or angled, regions that are not parallel to either the mounting regions 508 or the stimulation region 510, and that function to position the stimulation region 510 away from the mounting regions 508 and closer to a target stimulation region.

One or more mounting apertures 518 are disposed on each of the mounting regions 508. The one or more mounting apertures 518 are each configured and arranged for receiving a fastener (e.g., a bone screw, bolt, staples, sutures, or the like) 520. In at least some embodiments, one or more adhesives may be used in addition to, or in lieu of, extending the fastener 520 through the one or more mounting aperture 518. Any suitable number of mounting apertures 518 can be defined in the one or more mounting regions 508 including, for example, one, two, three, four, five, six, seven, eight, nine, ten, eleven, twelve, or more mounting apertures 518. In FIGS. 5A-5B (and in other figures), a single mounting aperture 518 is defined in each of the mounting regions 508.

In at least some embodiments, the mounting apertures 518 are positioned along the body such that the mounting apertures 518 align simultaneously with potential mounting surfaces of two different bony structures, such as two adjacent vertebrae 432. In at least some embodiments, the spacing between a first mounting aperture of the plurality of mounting apertures 518 and a second mounting aperture of the plurality of mounting apertures 518 is equal to the spacing between two adjacent vertebrae 432 of the patient.

One or more electrodes, such as electrode 526, are disposed on the orthopedic implant 504. In at least some embodiments, the one or more electrodes 526 are disposed on the stimulation region of the orthopedic implant. In at least some embodiments, the one or more electrodes 526 are disposed along a bottom surface of the one or more stimulation regions such that the stimulation region is disposed between the electrodes 526 and the mounting regions 508, thereby directing stimulation propagating from the electrodes 526 towards the target stimulation location.

Any suitable number of electrodes 526 can be disposed on the orthopedic implant including, for example, one, two, three, four, five, six, seven, eight, nine, ten, eleven, twelve, thirteen, fourteen, fifteen, sixteen, twenty, twenty-four, twenty-eight, thirty-two, forty, forty-eight, or more. In at least some embodiments, the one or more electrodes 526 extend outwardly from an outer surface of the orthopedic implant. In alternate embodiments, the one or more electrodes 526 are flush with, or inset from, the outer surface of the orthopedic implant. The one or more electrodes 526 can be formed in any suitable shape including, for example, round, oval, triangular, rectangular, or the like. It will be understood that the one or more electrodes 526 can be formed into other shapes, as well, either regular or irregular.

The one or more electrodes 526 are electrically coupled to the lead 502 via one or more conductors 528a disposed on or in the orthopedic implant. In at least some embodiments, the one or more conductors 528a are electrically coupled to one or more conductors 528b that are disposed along the body of the lead 502 and that electrically couple to the terminals disposed along the proximal end of the lead 502. In at least some alternate embodiments, the control module may couple directly to the orthopedic implant 504. In which case, the one or more conductors 528a electrically couple with conductors within the control module.

The one or more conductors 528a can be formed in any suitable manner including, for example, multi-filar conductive wires, single-filar conductive wires, conductive tracings, or the like. In at least some embodiments, the conductors 528a are formed along the body of the orthopedic implant as one or more conductive portions of the body.

In at least some embodiments, the body 506 of the orthopedic implant 504 is more rigid than the body of the lead 502. In at least some embodiments, the body 506 of the orthopedic implant 504 is formed from a material that maintains its shape once the orthopedic implant 504 is implanted in the patient. The orthopedic implant 504 can be formed from any rigid material suitable for implantation including, for example, titanium, stainless steel, one or more alloys, composite material, or the like.

In at least some embodiments, the body 506 of the orthopedic implant 504 is formed from a non-conductive material. In at least some embodiments, the body 506 of the orthopedic implant 504 is formed from a conductive material and includes one or more non-conductive layers of material disposed over one or more portions of an outer surface of the conductive material of the orthopedic implant 504.

The body 506 of the orthopedic implant 504 has a length 532 and a width 534. In at least some embodiments, the width 534 of the body 506 is greater than a diameter of the body of the lead 502. In at least some embodiments, the length 532 of the body 506 is smaller than a longitudinal length of the body of the lead 502. In at least some embodiments, the length 532 of the body 506 is substantially smaller than a longitudinal length of the body of the lead 502.

As shown in FIG. 5A, in at least some embodiments the stimulation region 510 is longitudinally aligned with the opposing mounting regions 508 along the length 532 of the body 506. As shown in FIG. 5A, in at least some embodiments the width 534 of the body 506 is constant along the entire length 532 of the body 506.

In FIGS. 5A-5B, the lead 502 is shown coupled to the body 506 of the orthopedic implant 504 along one of the mounting regions 508. In alternate embodiments, the lead 502 couples to the body 506 of the orthopedic implant 504 along the one or more stimulation regions 510, or along the one or more transition regions 512, or both.

In FIG. 5B, the stimulation region 510 is shown as being recessed from the mounting regions 508. When a particular DRG is the target stimulation location, it may be advantageous to form the stimulation region 510 as a recessed region of the body 606 to position the electrodes 526 closer to the DRG when the orthopedic implant 504 is mounted to two adjacent vertebrae 432 flanking the DRG.

FIG. 5C is a schematic top view of one embodiment of the orthopedic implant 504 anchored to two adjacent vertebrae 432a and 432b disposed in proximity to a target stimulation region. FIG. 5D is a schematic side view of one embodiment of the orthopedic implant 504 anchored to two adjacent vertebrae 432a and 432b flanking the targeted DRG 420a. The orthopedic implant 504 is mounted to the vertebrae 432a such that one of two fasteners 520 is passed through the mounting aperture of one of the two mounting regions 508 and into the vertebrae 432a, while the other of the two fasteners 520 is passed through the mounting aperture of the other of the two mounting regions 508 and into the vertebrae 432b.

In FIG. 5D, the stimulation region 510 of the body 506 of the orthopedic implant 504 is shown recessed from the mounting regions 508 such that the electrodes 526 are positioned in proximity to the DRG 420a. It will be understood that the orthopedic implant of FIGS. 5A-5D (as well as other orthopedic implants discussed herein) can be mounted to more than two vertebrae. It will also be understood that the orthopedic implant of FIGS. 5A-5D (as well as other orthopedic implants discussed herein) can be coupled to vertebrae that are not adjacent to one another.

Figure 6A:
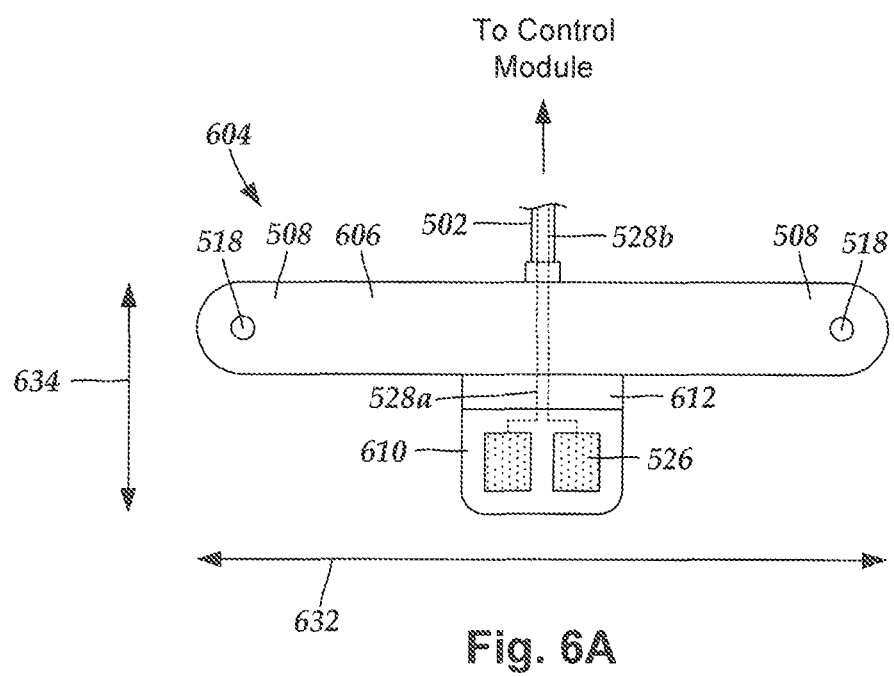
FIG. 6A is a schematic bottom view of a second embodiment of an orthopedic implant suitable for anchoring to one or more of the vertebrae of FIG. 4B, according to the invention.
Figure 6B:
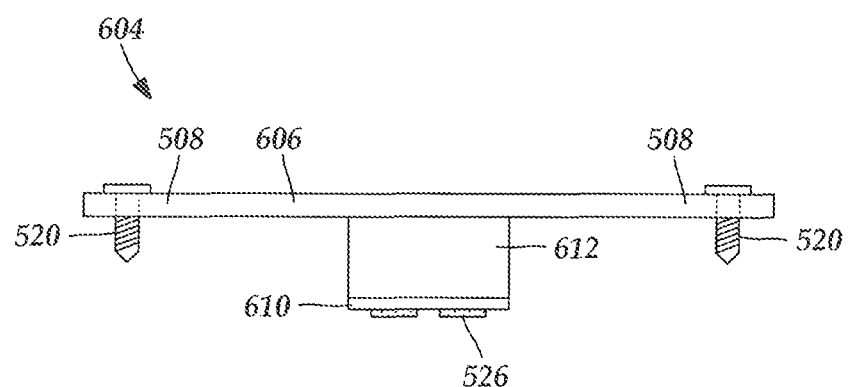
FIG. 6B is a schematic side view of one embodiment of the orthopedic implant of FIG. 6A, according to the invention.

In at least some embodiments, the one or more stimulation regions are longitudinally offset from the opposing mounting regions. FIG. 6A is a schematic bottom view of a second embodiment of the distal end of the body of the lead 502 coupled to an orthopedic implant 604. FIG. 6B is a schematic side view of one embodiment of the distal end of the body of the lead 502 coupled to the orthopedic implant 604. The orthopedic implant 604 includes an elongated body 606 with the mounting regions 508 disposed on opposing ends of the body 606 and a stimulation region 610 disposed therebetween. In at least some embodiments, the stimulation region 610 is disposed between the mounting regions 508 such that the stimulation region 610 is longitudinally offset from the opposing mounting regions 508.

In FIGS. 6A-6B, the mounting regions 508 are shown coupled to the stimulation region 610 via one or more transition regions 612. In at least some embodiments, the mounting regions 508 are planar. In at least some embodiments, the stimulation region 610 is planar. In FIGS. 6A-6B, the mounting regions 508 and the stimulation region 610 are shown as extending parallel to one another, while the transition region 612 is shown as a bent (or angled) region that is not parallel to either the mounting regions 508 or the stimulation region 610, and that functions to position the stimulation region 610 away from the mounting regions 508 and closer to a target stimulation region.

One or more electrodes, such as electrode 526, are disposed on the orthopedic implant 604. In at least some embodiments, the one or more electrodes 526 are disposed on the stimulation region of the orthopedic implant. In at least some embodiments, the one or more electrodes 526 are disposed along a bottom surface of the one or more stimulation regions such that the stimulation region is disposed between the electrodes 526 and the mounting regions 508, thereby directing stimulation propagating from the electrodes 526 towards the target stimulation region.

The one or more electrodes 526 are electrically coupled to the lead 502 via one or more conductors 528a disposed on or in the orthopedic implant. In at least some embodiments, the one or more conductors 528a are electrically coupled to one or more conductors 528b that are disposed along the body of the lead 502 and that electrically couple to the terminals disposed along the proximal end of the lead 502. In at least some alternate embodiments, the control module may couple directly to the orthopedic implant 504. In which case, the one or more conductors 528a electrically couple with conductors within the control module.

The one or more conductors 528a can be formed in any suitable manner including, for example, multi-filar conductive wires, single-filar conductive wires, conductive tracings, or the like. In at least some embodiments, the conductors 528a are formed along the body of the orthopedic implant as one or more conductive portions of the body.

In at least some embodiments, the body 606 of the orthopedic implant 604 is more rigid than the body of the lead 502. In at least some embodiments, the body 606 of the orthopedic implant 604 is formed from a material that maintains its shape once the orthopedic implant 604 is implanted in the patient. The orthopedic implant 604 can be formed from any rigid material suitable for implantation including, for example, titanium, stainless steel, one or more alloys, composite material, or the like. In at least some embodiments, the body 606 of the orthopedic implant 604 is formed from a non-conductive material. In at least some embodiments, the body 606 of the orthopedic implant 604 is formed from a conductive material and includes one or more non-conductive layers of material disposed over one or more portions of an outer surface of the conductive material of the orthopedic implant 604.

The body 606 of the orthopedic implant 604 has a length 632 and a width 634. In at least some embodiments, the width 634 of the body 606 is greater than a diameter of the body of the lead 502. In at least some embodiments, the length 632 of the body 606 is smaller than a longitudinal length of the body of the lead 502. As shown in FIG. 6A, in at least some embodiments the stimulation region 610 is longitudinally offset from the mounting regions 508. In at least some embodiments, the stimulation region 610 or the one or more transition regions 612 extend from a side surface one (or both) of the mounting regions 508.

In FIG. 6B, the stimulation region 610 is shown as being recessed from the mounting region 508. When a particular DRG is the target stimulation location, it may be advantageous to form the stimulation region 610 as a recessed region of the body 606 to position the electrodes 526 closer to the DRG when the orthopedic implant 604 is mounted to two adjacent vertebrae 432 flanking the DRG.

Figures 6C, 6D:
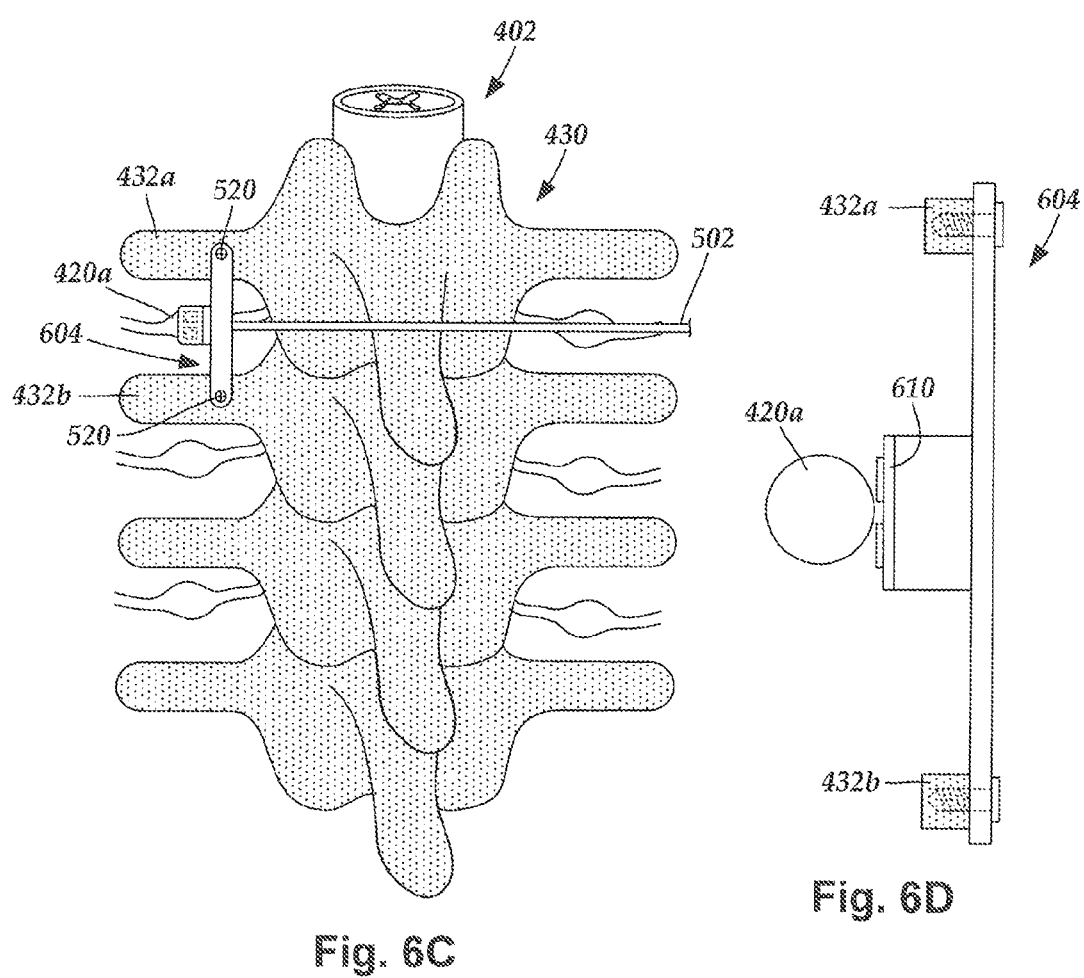
FIG. 6C is a schematic top view of one embodiment of the orthopedic implant of FIG. 6A anchored to two of the vertebrae of FIG. 4B, according to the invention.
FIG. 6D is a schematic side view of one embodiment of the orthopedic implant of FIG. 6A anchored to two of the vertebrae of FIG. 4B, according to the invention.

FIG. 6C is a schematic top view of one embodiment of the orthopedic implant 604 anchored to two adjacent vertebrae 432a and 432b disposed in proximity to a target stimulation region. FIG. 6D is a schematic side view of one embodiment of the orthopedic implant 604 anchored to two adjacent vertebrae 432a and 432b flanking the targeted DRG 420a. The orthopedic implant 604 is mounted to the vertebrae 432a such that one of two fasteners 520 is passed through the mounting aperture of one of the two mounting regions 508 and into the vertebrae 432a, while the other of the two fasteners 520 is passed through the mounting aperture of the other of the two mounting regions 508 and into the vertebrae 432b.

In FIG. 6D, the stimulation region 610 of the body 606 of the orthopedic implant 604 is shown recessed from the mounting region 508 such that the electrodes 526 are positioned in proximity to the DRG 420a. It will be understood that the orthopedic implant of FIGS. 6A-6D (as well as other orthopedic implants discussed herein) can be mounted to more than two vertebrae. It will also be understood that the orthopedic implant of FIGS. 6A-6D (as well as other orthopedic implants discussed herein) can be coupled to vertebrae that are not adjacent to one another.

Figure 7A:
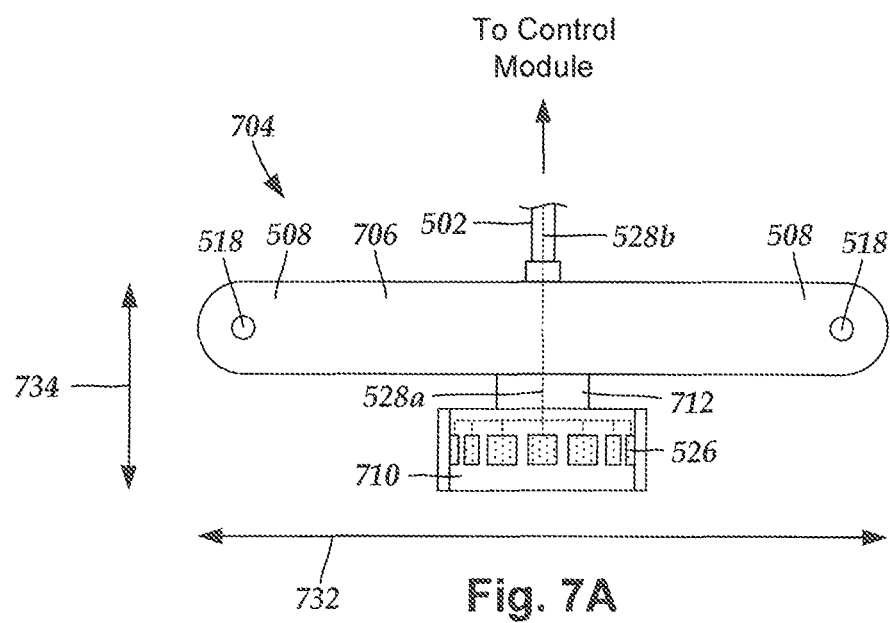
FIG. 7A is a schematic bottom view of a third embodiment of an orthopedic implant suitable for anchoring to one or more of the vertebrae of FIG. 4B, according to the invention.
Figure 7B:
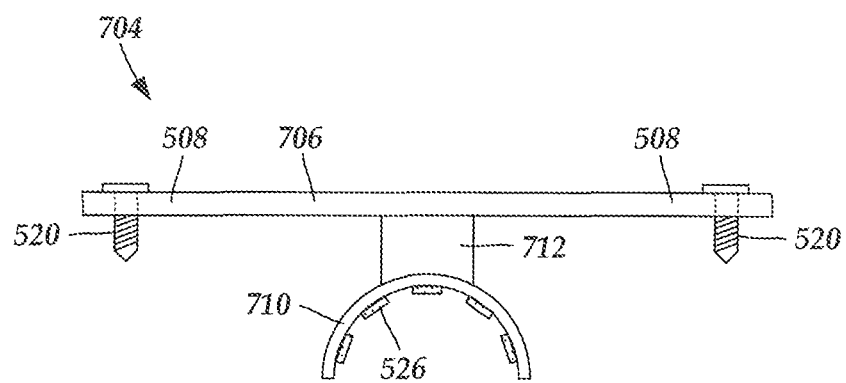
FIG. 7B is a schematic side view of one embodiment of the orthopedic implant of FIG. 7A, according to the invention.

In at least some embodiments, the one or more stimulation regions are arc-shaped. FIG. 7A is a schematic bottom view of a third embodiment of a distal end of the body of the lead 502 coupled to an orthopedic implant 704. FIG. 7B is a schematic side view of one embodiment of the distal end of the body of the lead 502 coupled to the orthopedic implant 704.

The orthopedic implant 704 includes an elongated body 706 with the mounting regions 508 disposed on opposing ends of the body 706 and a stimulation region 710 disposed therebetween. In at least some embodiments, the stimulation region 710 is disposed between the mounting regions 508 such that the stimulation region 710 is longitudinally offset from the opposing mounting regions 508.

In FIGS. 7A-7B, the mounting regions 508 are shown coupled to the stimulation region 710 via one or more transition regions 712. In at least some embodiments, the mounting regions 508 are planar. In FIGS. 7A-7B, the stimulation region 710 is shown as being arc-shaped, such that the target stimulation region can be disposed within the arc formed by the stimulation region 710. In at least some embodiments, the transition region 712 is a bent (or angled) region that functions to position the stimulation region 710 away from the mounting regions 508 and closer to a target stimulation location.

One or more electrodes, such as electrode 526, are disposed on the orthopedic implant 704. In at least some embodiments, the one or more electrodes 526 are disposed on the stimulation region of the orthopedic implant. In at least some embodiments, the one or more electrodes 526 are disposed along a bottom surface of the stimulation region (e.g., on an inner surface of the arc formed by the stimulation region) such that the stimulation region is disposed between the electrodes 526 and the mounting regions 508, thereby directing stimulation propagating from the electrodes 526 towards the target stimulation location.

The one or more electrodes 526 are electrically coupled to the lead 502 via one or more conductors 528a disposed on or in the orthopedic implant. In at least some embodiments, the one or more conductors 528a are electrically coupled to one or more conductors 528b that are disposed along the body of the lead 502 and that electrically couple to the terminals disposed along the proximal end of the lead 502. In at least some alternate embodiments, the control module may couple directly to the orthopedic implant 504. In which case, the one or more conductors 528a electrically couple with conductors within the control module.

In at least some embodiments, the body 706 of the orthopedic implant 704 is more rigid than the body of the lead 502. In at least some embodiments, the body 706 of the orthopedic implant 704 is formed from a material that maintains its shape once the orthopedic implant 704 is implanted in the patient. The orthopedic implant 704 can be formed from any rigid material suitable for implantation including, for example, titanium, stainless steel, one or more alloys, composite material, or the like. In at least some embodiments, the body 706 of the orthopedic implant 704 is formed from a non-conductive material. In at least some embodiments, the body 706 of the orthopedic implant 704 is formed from a conductive material and includes one or more non-conductive layers of material disposed over at least one or more portions of an outer surface of the conductive material of the orthopedic implant 704.

The body 706 of the orthopedic implant 704 has a length 732 and a width 734. In at least some embodiments, the width 734 of the body 706 is greater than a diameter of the body of the lead 502. In at least some embodiments, the length 732 of the body 706 is smaller than a longitudinal length of the body of the lead 502. As shown in FIG. 7A, in at least some embodiments the stimulation region 710 longitudinally offset from the mounting regions 508. In at least some embodiments, the stimulation region 710 or the one or more transition regions 712 extend from a side surface one (or both) of the mounting regions 508.

In FIG. 7B, the stimulation region 710 is shown as being recessed from the mounting region 508. When a particular DRG is the target stimulation location, it may be advantageous to form the stimulation region 710 as a recessed region of the body 706 to position the electrodes 526 closer to the DRG when the orthopedic implant 704 is mounted to two adjacent vertebrae 432 flanking the DRG.

FIG. 7C is a schematic top view of one embodiment of the orthopedic implant 704 anchored to two adjacent vertebrae 432a and 432b disposed in proximity to a target stimulation region. FIG. 7D is a schematic side view of one embodiment of the orthopedic implant 704 anchored to two adjacent vertebrae 432a and 432b flanking the targeted DRG 420a. The orthopedic implant 704 is mounted to the vertebrae 432a such that one of two fasteners 520 is passed through the mounting aperture of one of the two mounting regions 508 and into the vertebrae 432a, while the other of the two fasteners 520 is passed through the mounting aperture of the other of the two mounting regions 508 and into the vertebrae 432b.

In FIG. 7D, the stimulation region 710 of the body 706 of the orthopedic implant 704 is shown recessed from the mounting region 508 such that the electrodes 526 are positioned in proximity to the DRG 420a. It will be understood that the orthopedic implant of FIGS. 7A-7D (as well as other orthopedic implants discussed herein) can be mounted to more than two vertebrae. It will also be understood that the orthopedic implant of FIGS. 7A-7D (as well as other orthopedic implants discussed herein) can be coupled to vertebrae that are not adjacent to one another.

In at least some embodiments, the orthopedic implant is configured and arranged to mount to a single bony structure. FIG. 8A is a schematic side view of a fourth embodiment of a distal end of a body of the lead 502 coupled to an orthopedic implant 804. In at least some embodiments, the orthopedic implant 804 is formed as an elongated enhanced fastener (e.g., a bone screw, bolt, staple, or the like) 820. The enhanced fastener 820 includes a head 840 and a shaft 842 coupled to the head 840 at one end of the shaft 842. The shaft 842 has a length 832 and includes a tip 844 opposite to the head 840. The tip 844 is configured and arranged to penetrate a bony structure. In at least some embodiments, the enhanced fastener 804 includes one or more threads 846 extending along the shaft 842. The one or more threads 846 may facilitate penetration of the bony structure, or anchoring of the enhanced fastener 804 to the bony structure, or both.

One or more electrodes 526 are disposed along the shaft 842 in proximity to the tip 844 of the enhanced fastener 820. Alternately, the tip 844 itself may be formed as an electrode. The one or more electrodes 526 are electrically coupled to the lead 502 via one or more conductors 528*a* disposed on or in the orthopedic implant. In at least some embodiments, the one or more conductors 528*a* are electrically coupled to one or more conductors 528*b* that are disposed along the body of the lead 502 and that electrically couple to the terminals disposed along the proximal end of the lead 502. In at least some alternate embodiments, the control module may couple directly to the orthopedic implant 504. In which case, the one or more conductors 528*a* electrically couple with conductors within the control module.

In at least some embodiments, the length 832 of the shaft 842 is greater than a thickness of the bony structure to which the enhanced fastener 804 is configured to anchor. In which case, the enhanced fastener 804 may be configured and arranged for extending completely through the bony structure when the enhanced fastener 804 is anchored to the bony structure such that the tip 844 of the enhanced fastener 804 extends outwardly from a surface of the bony structure.

FIG. 8B is a schematic side view of one embodiment of the orthopedic implant 804 anchored to the vertebra 432*a* such that the shaft 842 extends completely through the vertebrae 432*a* with the tip 844 extending outwardly from a surface of the vertebra 432*a* that is opposite from the head 840. In FIG. 8B, the one or more electrodes 526 are disposed along the tip 844 and are positioned in proximity to the DRG 420*a*. In at least some embodiments, the one or more electrodes 526 are configured and arranged for coupling to the tip 844 after the enhanced fastener 804 is anchored to the bony structure and extended therethrough. In which case, the one or more electrodes 804 can be either removably or permanently coupled to the tip 844 using any suitable technique (e.g., adhesive, screw, bolt, snap, sutures, interference fit, or the like or combinations thereof).

As shown in FIG. 8B, in at least some embodiments when the enhanced fastener 804 is anchored to the bony structure the head 840 of the enhanced fastener 804 extends from a first surface of the bony structure while the tip 844 extends outwardly from a second surface of the bony structure, opposite to the first surface. Alternately, in at least some embodiments when the enhanced fastener 804 is fastened to the bony structure the head 840 of the enhanced fastener 804 is flush with, or inset from, the first surface of the bony structure while the tip 844 extends outwardly from the second surface of the bony structure.

In at least some embodiments, the one or more electrodes 526 are bendable. FIG. 8C is a schematic side view of another embodiment of the orthopedic implant 804 anchored to one of the vertebrae 432*a*. FIG. 8D is a schematic top view of the embodiment of the orthopedic implant 804 shown in FIG. 8C anchored to one of the vertebrae 432*a*. As shown in FIGS. 8C and 8D, the one or more electrodes 526 are configured and arranged to bend. In which case, the one or more electrodes 526 can be bent so that the one or more electrodes 526 are disposed in proximity to the target stimulation region (e.g., the DRG, or the like) 420*a*.

It may be advantageous for the one or more electrodes to be bendable so that the one or more electrodes 526 can be positioned more closely to the target stimulation region after the enhanced fastener 804 is anchored to the bony structure, thereby reducing the potential for undesirably stimulating non-targeted tissue in proximity to the target stimulation location.

Figure 9A:
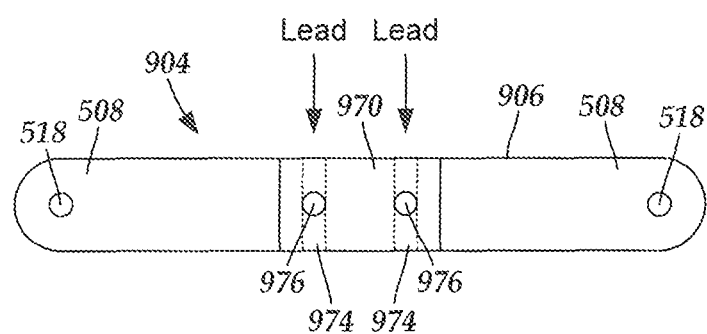
FIG. 9A is a schematic top view of a fifth embodiment of an orthopedic implant that includes an anchoring unit suitable for anchoring one or more leads to one or more of the vertebrae of FIG. 4B, according to the invention.
Figure 9B:
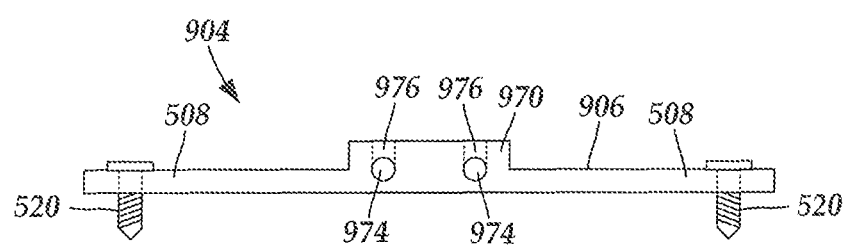
FIG. 9B is a schematic side view of one embodiment of the orthopedic implant of FIG. 9A, according to the invention.

In at least some embodiments, instead of disposing one or more electrodes along a body of the orthopedic implant (as shown and discussed with reference to FIGS. 5A-8D), the orthopedic implant is configured and arranged to retain one or more leads. FIG. 9A is a schematic top view of a fifth embodiment of an orthopedic implant 904 that includes an anchoring unit suitable for anchoring one or more leads to one or more of the vertebrae 432. FIG. 9B is a schematic side view of one embodiment of the orthopedic implant 904. In at least some embodiments, the orthopedic implant 904 is configured and arranged to anchor one or more leads to the orthopedic implant 904 such that electrodes disposed along the one or more leads can be positioned in proximity to a target stimulation location (e.g., a DRG, or the like).

The orthopedic implant 904 includes an elongated body 906 having one or more mounting regions 508 with mounting apertures 518 for mounting the orthopedic implant 904 to one or more bony structures. The orthopedic implant 904 also includes one or more lead anchoring regions 970 for anchoring the one or more leads to the orthopedic implant 904.

In at least some embodiments, the one or more lead anchoring regions 970 are disposed between two or more mounting regions 508. In at least some embodiments, the one or more lead anchoring regions 970 are disposed between the mounting regions 508 such that the one or more lead anchoring regions 970 are aligned along a longitudinal axis with the two or more mounting regions 508 disposed on opposing ends of the body 906. In at least some other embodiments, the one or more lead anchoring regions 970 are longitudinally offset from the mounting regions 508. In at least some embodiments, the body 906 additionally includes one or more transition regions coupling the one or more mounting regions 508 to the one or more lead anchoring regions 508.

In at least some embodiments, the one or more lead anchoring regions 970 are recessed from the one or more mounting region 508. When a particular DRG is the target stimulation location, it may be advantageous to form the one or more anchoring regions 970 as a recessed region of the body 906 in order to position the electrodes 526 closer to the DRG when the orthopedic implant 904 is mounted to two adjacent vertebrae 432 flanking the DRG.

In at least some embodiments, the body 906 of the orthopedic implant 904 is formed from a material that maintains its shape once the orthopedic implant 904 is implanted in the patient. The orthopedic implant 904 can be formed from any rigid material suitable for implantation including, for example, titanium, stainless steel, one or more alloys, composite material, or the like. In at least some embodiments, the body 906 of the orthopedic implant 904 is formed from a non-conductive material. In at least some embodiments, the body 906 of the orthopedic implant 904 is formed from a conductive material and includes one or more non-conductive layers of material disposed over at least one or more portions of an outer surface of the conductive material of the orthopedic implant 904.

In at least some embodiments, the one or more lead anchoring regions 970 are configured and arranged to anchor one or more leads to the orthopedic implant 904 such that electrodes disposed on the one or more leads can be positioned in proximity to a target stimulation location (e.g., a DRG, or the like).

In at least some embodiments, the one or more lead anchoring regions 970 each includes one or more lead lumens 974, where each of the one or more lead lumens 974 is configured and arranged to receive a portion of a lead. In at least some embodiments, the one or more lead anchoring regions 970 each includes one or more fastener lumens 976 that intersect with the one or more lead lumens 974 and that are configured and arranged to receive a fastener (e.g., a screw, pin, clamp, latch, lug, nail, bolt, dowel, rod, rivet, or the like or combinations thereof) for fastening against a portion of a lead when the lead is inserted into the lead lumen 974. Examples of anchoring regions configured and arranged for receiving portions of leads are found in, for example, U.S. Patent Application Publication No. 2010/0274336; 2011/0178573; and 2012/0185027, all of which are incorporated by reference.

In at least some embodiments, the orthopedic implant 904 is configured and arranged to anchor one or more percutaneous leads (see e.g., FIG. 2) to the one or more bony structures. FIG. 9C is a schematic top view of one embodiment of distal ends of two percutaneous leads 980a and 980b extending through the lead lumens 974. Each of the percutaneous leads 980a and 980b includes a plurality of terminals (see e.g., terminals 310 of FIGS. 3A-3C) disposed at proximal ends of the percutaneous leads 980a and 980b. Fasteners 978 (e.g., screws, pins, clamps, latches, lugs, nails, bolts, dowels, rods, rivets, or the like or combinations thereof) are extended along the fastener lumens 976 and used to fasten the percutaneous leads 980a and 980b to the orthopedic implant 904.

A plurality of electrodes, such as electrodes 982a and 982b, are disposed along the distal ends of the percutaneous leads 980a and 980b, respectively. As shown in FIG. 9C, in at least some embodiments the one or more lead lumens 974 are configured and arranged to receive a portion of a distal end of the percutaneous leads 980a and 980b. In at least some embodiments, the one or more lead lumens 974 are configured and arranged to receive a portion of the distal end of the percutaneous leads 980a and 980b proximal to the plurality of electrodes 982a and 982b.

The electrodes 982a and 982b can be any suitable shape, such as ring-shaped, cuff-shaped, arc-shaped or segmented. Examples of leads with segmented electrodes include U.S. Pat. Nos. 8,295,944; and 8,391,985; U.S. Patent Application Publications Nos. 2010/0268298; 2011/0005069; 2011/0078900; 2011/0130817; 2011/0130818; 2011/0238129; 2011/0313500; 2012/0016378; 2012/0046710; 2012/0165911; 2012/0197375; 2012/0203316; 2012/0203320; 2012/0203321, all of which are incorporated herein by reference. It may be advantageous for the electrodes 982a and 982b to be shaped such that stimulation energy propagated from the electrodes 982a and 982b is directed primarily towards the target stimulation location. For example, it may be advantageous to form the electrodes 982a and 982b such that they do not extend completely around the circumference of the body of the percutaneous leads 980a and 980b.

In at least some embodiments that use directional electrodes, the proximal ends of the bodies of the percutaneous leads 980a and 980b include markers identifying the directionality of the electrodes 982a and 982b. The markers may be used to facilitate implantation by enabling a practitioner to be able to recognize the orientation of the electrodes in the implanted leads by visually inspecting the markers disposed at the proximal ends of the leads.

Figure 9D:
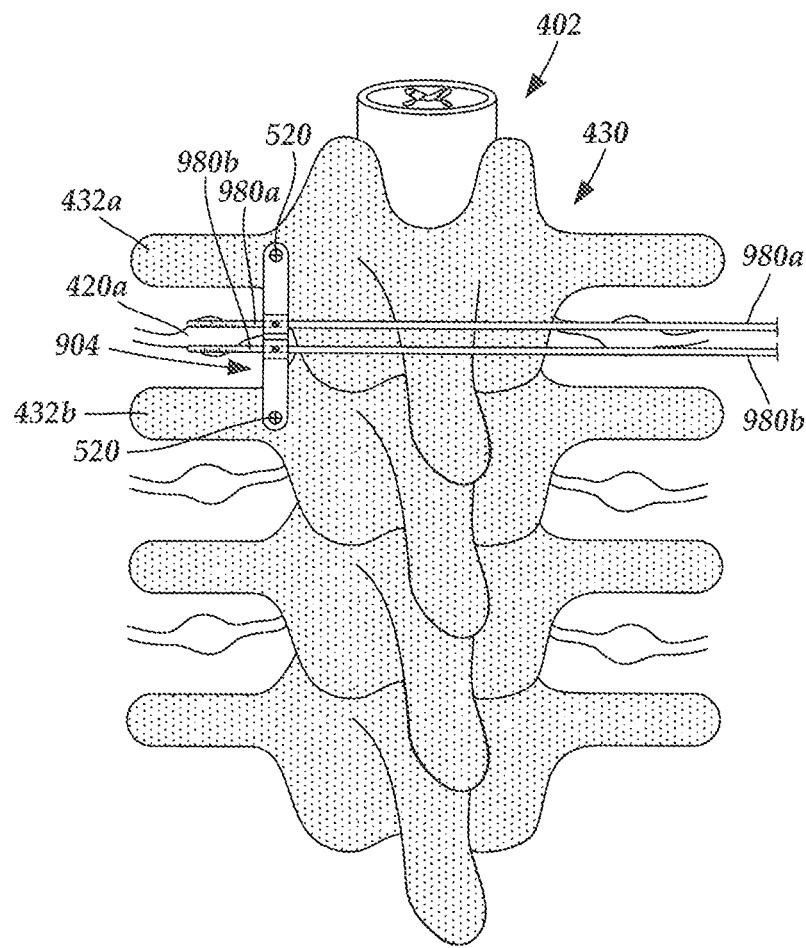
FIG. 9D is a schematic top view of one embodiment of the two percutaneous leads of FIG. 9C fastened to the orthopedic implant of FIG. 9A, and the orthopedic implant anchored to two of the vertebrae of FIG. 4B, according to the invention.

FIG. 9D is a schematic top view of one embodiment of the orthopedic implant 904 anchored to two of the vertebrae 432a and 432b by fasteners 520. Two percutaneous leads 980a and 980b are fastened to the orthopedic implant 904 such that the electrodes 982a and 982b of the percutaneous leads 980a and 980b, respectively, are disposed in proximity to the DRG 420a. It will be understood that the orthopedic implant can be anchored to the one or more bony structures either before or after the one or more leads are fastened to the orthopedic implant.

In at least some embodiments, the orthopedic implant 904 is configured and arranged to anchor one or more paddle leads (see e.g., FIG. 1) to the one or more bony structures. FIG. 9E is a schematic top view of one embodiment of a paddle lead 990 fastened to the orthopedic implant 904. The paddle lead 990 includes a paddle body 992 and a plurality of lead bodies 994 coupled to the paddle body 992. A plurality of electrodes, including electrode 996, are disposed on the paddle body 992.

Each of the lead bodies 994 includes a plurality of terminals (see e.g., terminals 310 of FIGS. 3A-3C) disposed at proximal ends of the lead bodies 994. The lead bodies 994 of the paddle lead 990 are shown in FIG. 9E extending through the lead lumens 974 and fastened to the orthopedic implant 904 by fasteners 978 extended along the fastener lumens 976.

In FIG. 9E, the electrodes 996 are shown disposed along a bottom surface of the paddle body 992. It may be advantageous for the electrodes 996 to be oriented such that stimulation energy propagated from the electrodes 996 is directed towards the target stimulation location. For example, when the orthopedic implant 904 is anchored to a bony structure disposed above the target stimulation location, it may be advantageous to orient the lead(s) such that the electrodes face downward, towards the target stimulation location, such as is shown in FIG. 9D.

In FIGS. 9A-9E the orthopedic implant 904 is shown with an elongated body 906 configured and arranged to mount to, and extend between, two bony structures. In at least some embodiments, the orthopedic implant 904 may be configured and arranged to mount to a single bony structure. For example, in at least some embodiments the one or more lead anchoring regions 970 are coupled to the enhanced fastener 804.

Figure 10:
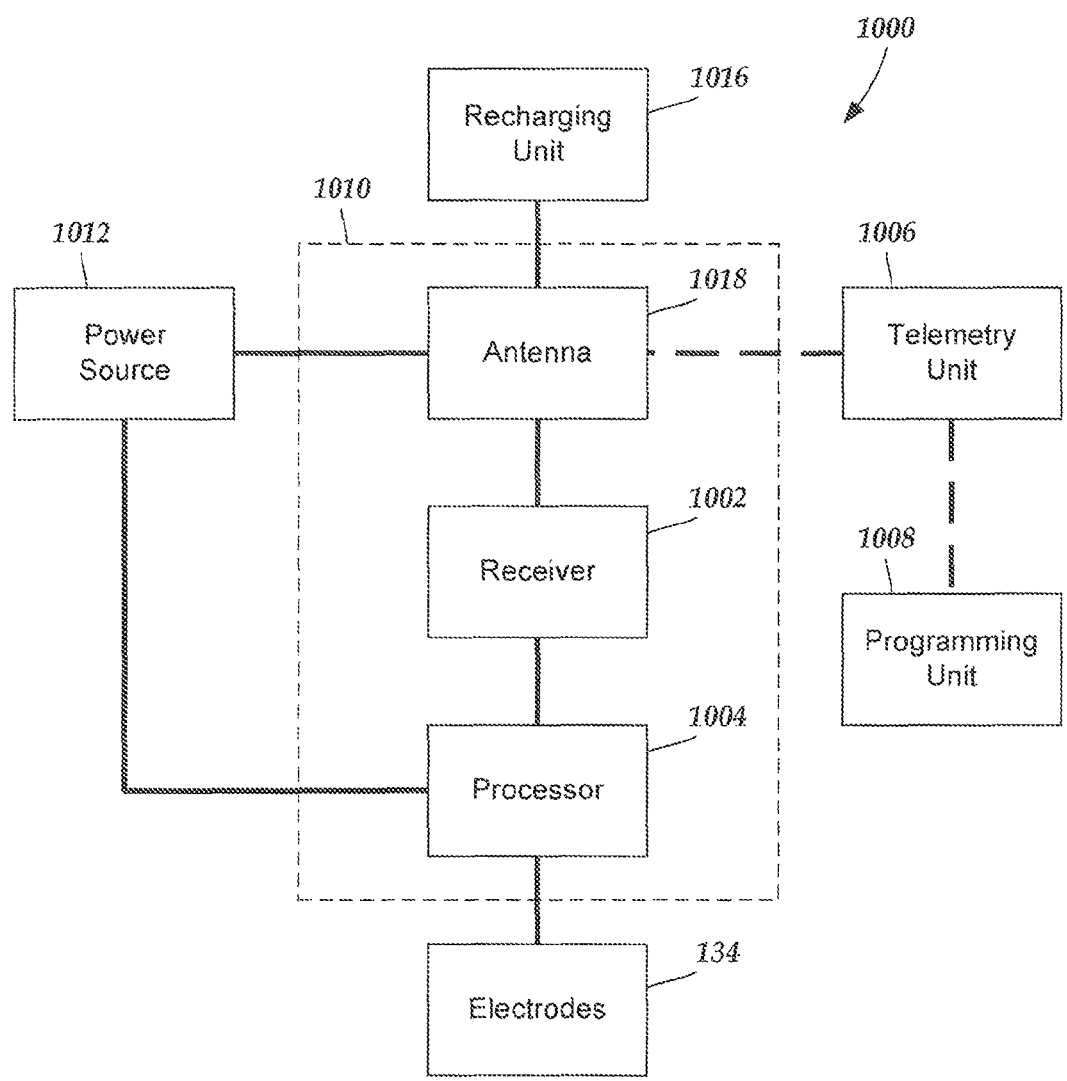
FIG. 10 is a schematic overview of one embodiment of components of an electrical stimulation system, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchoring assembly for providing electrical stimulation, the lead anchoring assembly comprising:
   an orthopedic implant configured and arranged to receive a distal end of a lead body of a first lead, the orthopedic implant configured and arranged for anchoring to at least one bony structure, the orthopedic implant comprising
      an orthopedic implant body having a first end, a second end opposite to the first end, a first side, a second side opposite to the first side, a top surface, and a bottom surface opposite to the top surface,
      at least one mounting region disposed along the orthopedic implant body, the at least one first mounting region configured and arranged for anchoring the orthopedic implant to the at least one bony structure,
      a lead anchoring region disposed along the orthopedic implant body, the lead anchoring region configured and arranged for receiving the first lead and for fastening the first lead to the orthopedic implant, and
      a first lead lumen defined in the lead anchoring region and forming a continuous opening extending between the opposing first and second sides of the orthopedic implant body, the first lead lumen configured and arranged to receive the first lead.

2. The lead anchoring assembly of claim 1, wherein the lead anchoring region defines a first fastener lumen defining a continuous opening extending between the top surface of the orthopedic implant body and the first lead lumen.

3. A lead assembly comprising:
   the lead anchoring assembly of claim 2; and
   a first lead comprising
      a lead body with a proximal end, a distal end, and a longitudinal length;
      a plurality of electrodes disposed along the distal end of the lead body;
      a plurality of terminals disposed along the proximal end of the lead body; and
      a plurality of conductors, each conductor electrically coupling at least one of the plurality of electrodes to at least one of the plurality of terminals.

4. The lead assembly of claim 3, further comprising a first fastener configured and arranged for insertion into the first fastener lumen, the first fastener configured and arranged for fastening the first lead to the orthopedic implant when the first lead is disposed in the first lead lumen.

5. The lead assembly of claim 3, wherein the first lead is one of a percutaneous lead or a paddle lead.

6. The lead anchoring assembly of claim 1, wherein the lead anchoring region further defines a second lead lumen configured and arranged to receive a second lead, the second lead lumen defining a continuous opening extending between the first side and the second side of the orthopedic implant body, and a second fastener lumen defining a continuous opening extending between the top surface of the orthopedic implant body and the second lead lumen.

7. The lead anchoring assembly of claim 1, wherein the at least one mounting region comprises a first mounting region disposed along the first end of the orthopedic implant body and a second mounting region disposed along the second end of the orthopedic implant body.

8. The lead anchoring assembly of claim 7, wherein the orthopedic implant body further comprises
   at least one first mounting aperture defined along the first mounting region, the at least one first mounting aperture configured and arranged for receiving at least one first mounting fastener for anchoring the orthopedic implant to the at least one bony structure; and at least one second mounting aperture defined along the second mounting region, the at least one second mounting aperture configured and arranged for receiving at least one second mounting fastener for anchoring the orthopedic implant to the at least one bony structure.

9. The lead anchoring assembly of claim 8, further comprising at least one first mounting fastener configured and arranged for passing through the at least one first mounting aperture and for anchoring the orthopedic implant to the at least one bony structure: and at least one second mounting fastener configured and arranged for passing through the at least one second mounting aperture and for anchoring the orthopedic implant to the at least one bony structure.

10. The lead anchoring assembly of claim 7, wherein the lead anchoring region is disposed along the orthopedic implant body between the first mounting region and the second mounting region.

11. The lead anchoring assembly of claim 1, wherein the orthopedic implant is configured and arranged for anchoring to a plurality of bony structures, the plurality of bony structures comprising a first bony structure and a second bony structure.

12. The lead anchoring assembly of claim 1, wherein the orthopedic implant body comprises at least one transition region coupling the at least one mounting region to the lead anchoring region.

13. The lead anchoring assembly of claim 1, wherein the lead anchoring region is recessed from the at least one mounting region.

14. A method for implanting a lead assembly into a patient, the method comprising:

providing a lead anchoring assembly, the lead anchoring assembly comprising an orthopedic implant configured and arranged to receive a distal end of a lead body of a first lead the orthopedic implant configured and arranged for anchoring to at least one bony structure, the orthopedic implant comprising an orthopedic implant body having a first end a second end opposite to the first end a first side, a second side opposite to the first side, a top surface, and a bottom surface opposite to the top surface, at least one mounting region disposed along the orthopedic implant body, the at least one first mounting region configured and arranged for anchoring the orthopedic implant to the at least one bony structure, and a lead anchoring region disposed along the orthopedic implant body, the lead anchoring region configured and arranged for receiving the first lead and for fastening the first lead to the orthopedic implant;

anchoring the at least one mounting region to the at least one bony structure;

inserting a first lead into the lead anchoring region; and fastening the first lead to the lead anchoring region of the orthopedic implant of the lead assembly.

15. An implantable lead assembly for providing electrical stimulation to a patient, the lead assembly comprising:

a lead body having a proximal end, a distal end, and a longitudinal length;

at least one terminal disposed along the proximal end of the lead body;

an orthopedic implant coupled to the distal end of the lead body, the orthopedic implant configured and arranged for anchoring to at least one bony structure, the orthopedic implant comprising a head configured and arranged for receiving a fastening tool, an elongated shaft coupled to the head, the shaft having a first end and an opposing second end, wherein the first end couples to the head, and a tip disposed on the second end of the shaft, the tip configured and arranged to anchor to the at least one bony structure;

at least one electrode disposed along the tip of the orthopedic implant; and at least one conductor electrically coupling the at least one terminal to the at least one electrode.

16. The lead assembly of claim 15, wherein the at least one electrode is bendable.

17. A method for implanting a lead assembly into a patient, the method comprising:

providing the lead assembly of claim 15;

inserting the tip of the orthopedic implant of the lead assembly into a first surface of at least one bony structure; and extending the tip outwardly from an opposing second outer surface of the at least one bony structure.

18. An electrical stimulating system comprising:

the lead assembly of claim 3;

a control module electrically coupled to the plurality of electrodes of the first lead of the lead assembly, the control module comprising a housing, and an electronic subassembly disposed in the housing; and a connector assembly for receiving the first lead, the connector assembly comprising a connector housing defining at least one port configured and arranged for receiving the proximal end of the first lead, and a plurality of connector contacts disposed in the connector housing, the plurality of connector contacts configured and arranged to couple to the plurality of terminals when the proximal end of the first lead is received by the at least one port.

19. The lead assembly of claim 15, wherein the at least one electrode is removably coupled to the tip.

20. The lead assembly of claim 15, wherein the at least one electrode is permanently coupled to the tip.

* * * * *